United States Patent
Zhang et al.

(10) Patent No.: US 11,203,647 B2
(45) Date of Patent: Dec. 21, 2021

(54) DUAL-FUNCTION STARCH-BASED COMPOSITE NANOPARTICLES AS WELL AS PREPARATION METHOD AND APPLICATION THEREOF

(71) Applicant: HEFEI UNIVERSITY OF TECHNOLOGY, Hefei (CN)

(72) Inventors: Bao Zhang, Hefei (CN); Baocai Xu, Hefei (CN); Xiaomin Li, Hefei (CN); Peijun Li, Hefei (CN); Yi Pan, Hefei (CN); Ran Meng, Hefei (CN); Xiaolong Li, Anhui Province (CN); Wenjie Liu, Hefei (CN)

(73) Assignee: HEFEI UNIVERSITY OF TECHNOLOGY, Anhui (CN)

( * ) Notice: Subject to any disclaimer, the term of this patent is extended or adjusted under 35 U.S.C. 154(b) by 107 days.

(21) Appl. No.: 16/740,576

(22) Filed: Jan. 13, 2020

(65) Prior Publication Data

US 2021/0122835 A1     Apr. 29, 2021

Related U.S. Application Data

(63) Continuation of application No. PCT/CN2019/113153, filed on Oct. 25, 2019.

(51) Int. Cl.
| | |
|---|---|
| *C08B 30/18* | (2006.01) |
| *A61K 8/02* | (2006.01) |
| *A61K 9/51* | (2006.01) |
| *A61K 8/73* | (2006.01) |
| *A61K 8/35* | (2006.01) |

(52) U.S. Cl.
CPC .............. *C08B 30/18* (2013.01); *A61K 8/025* (2013.01); *A61K 8/35* (2013.01); *A61K 8/732* (2013.01); *A61K 8/736* (2013.01); *A61K 9/5161* (2013.01)

(58) Field of Classification Search
CPC ...... C08B 30/18; A61K 8/025; A61K 9/5161; A61K 8/736; A61K 8/35; A61K 8/732
See application file for complete search history.

(56) References Cited

U.S. PATENT DOCUMENTS 9,580,518 B2 *   2/2017   Jin ......................... C08B 30/18

OTHER PUBLICATIONS

P.L. Bragd, et al, Tempo-Mediated Oxidation of Polysaccharides: Survey of Methods and Applications, 27 Topics Catal. 49, 58 (Year: 2004).*
Binghua Sun, et al, Linear Dextrin as Curcumin Delivery System: Effect of Degree of Polymerization on the Functional Stability of Curcumin, 77 Food Hydrocoll. 911 (Year: 2018).*

* cited by examiner

*Primary Examiner* — Sean M Basquill
(74) *Attorney, Agent, or Firm* — PROI Intellectual Property US; Klaus Michael Schmid (57) ABSTRACT

The present application discloses dual-function starch-based composite nanoparticles as well as a preparation method and application thereof. The preparation method comprises: hydrolyzing starch to form linear dextrin, grading the linear dextrin by using an alcohol-alcohol gradient precipitation method to obtain linear dextrin having homogeneous molecular weight distribution; oxidizing the linear dextrin by adopting an oxidation system to obtain oxidized dextrin; carrying out complex reaction on the oxidized dextrin and curcumin to form an oxidized dextrin-curcumin complex; and forming an oxidized dextrin-curcumin/chitosan hydrochloride composite nanoparticles from the oxidized dextrin-curcumin complex and chitosan hydrochloride. The aqueous phase solution of the dual-function starch-based composite nanoparticles containing gel polysaccharide is uniformly mixed with primary emulsion, calcium ion induction is carried out on the obtained double emulsion to obtain double-emulsion gel.

8 Claims, 6 Drawing Sheets

DUAL-FUNCTION STARCH-BASED COMPOSITE NANOPARTICLES AS WELL AS PREPARATION METHOD AND APPLICATION THEREOF

TECHNICAL FIELD

The present application relates to dual-function starch-based composite nanoparticles and a preparation method thereof as well as application of the dual-function starch-based composite nanoparticles in preparation of stable $W_1/O/W_2$ double-emulsion gels, belonging to the technical field of starch deep processing.

BACKGROUND

The modern food industry pays more and more attention to functional food for improving human nutrition and health, and a large number of bioactive substances are widely applied to various food systems. However, the stability of most of these substances is poor, and the bioactive components are easily destroyed, thereby limiting their application in the food industry. Fat-soluble nutrients, including fat-soluble vitamins ($V_A$, $V_D$ and $V_E$), polyunsaturated fatty acids (EPA, DHA and CLA), carotenoids and hydrophobic plant polyphenols (tea polyphenols, curcumin and isoflavones, etc.), are easily oxidized and degraded due to their poor solubility, and features such as low bioavailability further limit their application in food. How to achieve effective addition of bioactive substances in food and maintain their bioactivity is a major technical problem in the current food industry.

The construction of Pickering emulsion (emulsion liquid obtained by using ultrafine solid particles as an emulsifier) delivery system stabilized by food-grade colloid particles is an important way to improve the stability and biological potency of liposoluble functional factors. However, unsaturated fatty acids and lipid bioactive substances in the emulsion are prone to oxidizing reaction in the process of storage. This not only causes the loss of essential fatty acids and bioactive substances, but also produces extremely harmful substances such as peroxides, aldehydes, ketones, alcohols, hydrocarbons and acids. These products change the sensory quality of food, such as flavor and color, and even have genetic and cellular toxicity. Ingestion of food containing lipid oxidized products can cause damage on human tissues and organs so as to seriously harm human health. A large number of studies have shown that an interface is a main place where emulsion is oxidized, and a pro-oxidant in a continuous phase can interact with the hydroperoxide of the emulsion droplet. Therefore, designing and constructing the interface structure with oxidation defense performance is an effective way to improve the oxidation stability of emulsion.

Double emulsion is a multiple emulsion consisting of smaller emulsion droplets. Compared with the traditional emulsion, the double emulsion has unique advantages in the aspects of research and development of microencapsulation, slow release and low-fat food because of its internal region partition. One main disadvantage of $W_1/O/W_2$ double emulsion is that the double emulsion is poor in stability, which limits its industrial application. The preparation of double emulsion using solid particles instead of at least one type of surfactant molecule provides a new strategy for improving the stability of double emulsion, which is conducive to expanding the application of double emulsion in industry.

Emulsion gel is a new structural emulsion in which dispersed droplets are immobilized in a tight gel network. Better protection is provided for active components based on an oil-water interface effect and a gel network structure. The release and absorption of active components can be regulated and controlled by changing the gel structure.

Based on this, the construction of nanoparticles having both oxidation resistance and interfacial stability and application thereof in preparation of double-emulsion gel have great significance in the aspects of improving the antioxidant activity of lipid and the stability of double emulsion.

SUMMARY

An major objective of the present application is to provide a dual-function starch-based composite nanoparticles and a preparation method thereof to overcome the defects of the prior art.

Another major objective of the present application is to provide $W_1/O/W_2$ double-emulsion gel prepared based on the above dual-function starch-based composite nanoparticles and a preparation method thereof.

Another major objective of the present application is to provide application of the above $W_1/O/W_2$ double-emulsion gel.

In order to realize the above objectives of the disclosure, the technical solution adopted by the present application includes:

An embodiment of the present application provides a preparation method of a dual-function starch-based composite nanoparticles, comprising:

hydrolyzing starch to form starch hydrolyzate, thereby obtaining linear dextrin;

grading the linear dextrin by using an alcohol-alcohol gradient precipitation method to obtain linear dextrin having homogeneous molecular weight distribution;

oxidizing the linear dextrin by adopting a TEMPO/NaClO/NaBr oxidation system to obtain oxidized dextrin;

performing complex reaction on a first mixed system containing oxidized dextrin and curcumin to form an oxidized dextrin-curcumin complex; and forming an oxidized dextrin-curcumin/chitosan hydrochloride composite nanoparticles from the oxidized dextrin-curcumin complex and chitosan hydrochloride through electrostatic complexing action so as to obtain the dual-function starch-based composite nanoparticles.

In some embodiments, the preparation method specifically comprises:

providing mixed solution containing 2,2,6,6-tetramethyl-1-piperidinyloxy free radical (namely TEMPO), NaBr and water; and mixing the mixed solution with the linear dextrin and regulating the pH value of the obtained second mixed system to 10~10.75, then adding NaClO and keeping the pH value of the second mixed system unchanged, and precipitating out the obtained oxidized dextrin when the oxidization degree of the linear dextrin is 30~90%.

In some embodiments, the preparation method specifically comprises:

providing ethanol solution containing curcumin;

providing water dispersion liquid containing the oxidized dextrin, heating for 30~45 min at 90~100° C., and then cooling to 65~80° C.;

uniformly mixing the ethanol solution containing curcumin with the water dispersion liquid containing the oxidized dextrin to form the first mixed system, carrying out complex reaction for 2~4 h at 65~80° C. to obtain the oxidized dextrin-curcumin complex.

In some embodiments, the preparation method specifically comprises: uniformly mixing the oxidized dextrin-curcumin complex with chitosan hydrochloride for 30~45 min in a mass ratio of (1:5)~(5:1) in a reaction system of 20~25° C. and pH of 4~4.5, and forming an oxidized dextrin-curcumin/chitosan hydrochloride composite nanoparticles through electrostatic complexing action.

Embodiments of the present application also provide the dual-function starch-based composite nanoparticles prepared by the above method.

Embodiments of the present application also provide a preparation method of double-emulsion gel, comprising:

preparing a dual-function starch-based composite nanoparticles according to the foregoing method;

uniformly mixing chloride, gelatin or ethanol or glucose with water to form a first aqueous phase solution, and uniformly mixing the first aqueous phase solution with an oil phase component to form primary emulsion;

uniformly mixing a second aqueous phase solution containing the dual-function starch-based composite nanoparticles with the primary emulsion by using high pressure homogenization and microfluidization technologies to obtain double emulsion containing gel polysaccharide; and carrying out water bath treatment on the double emulsion containing gel polysaccharide, adding $Ca^{2+}$ to induce crosslinking reaction of gel polysaccharide and cooling to obtain the double-emulsion gel.

Further, the preparation method comprises: shearing the mixed solution of the primary emulsion and the second aqueous phase solution by using the high pressure homogenization technology to form crude double emulsion, then further homogenizing the crude double emulsion 3~5 times under 103.4~121 MPa by using the high-pressure microfluidization technology to obtain the double emulsion.

Embodiments of the present application also provide the double-emulsion gel prepared by the above method.

Embodiments of the present application also provide use of the above double-emulsion gel in the fields of protection of nutrient components, delivery of drugs or preparation of cosmetics.

Compared with the prior art, the present application has the following advantages:

1) In the present application, renewable starch is used as a raw material to be deep processed, which can enlarge the application range of starch and meanwhile enriching the academic contents of the starch subject;

2) In the present application, alcohol-alcohol gradient precipitation grading is adopted to obtain linear dextrin having homogeneous polymerization degree, and therefore the method is simple and easily available, and TEMPO directed-site quantitative oxidation is adopted so as to retain the spiral cavity of dextrin, thereby facilitating the complex embedding effect of dextrin on curcumin;

3) In the present application, the composite nanoparticles are prepared by using an electrostatic interaction method, reaction conditions are mild, the method is simple, and the obtained nanoparticles have appreciate wettability and spherical shape as well as good emulsion performance and interface stability performance;

4) In the present application, the double-emulsion gel is prepared by using the composite nanoparticles, the emulsion is stabilized by an interface layer formed from particles and a gel network, and the double-emulsion gel has higher stability, and has good oxidation resistance and long-term storage stability (180 days), as compared with the emulsion stabilized by a surfactant.

5) In the present application, reaction conditions are mild, the preparation method is simple, large-scale production is easily realized, and the double-emulsion gel can be applied to the fields of protection of nutrient components, delivery of drugs and preparation of cosmetics.

BRIEF DESCRIPTION OF THE DRAWINGS

For more clearly illustrating embodiments of the present application or technical solution in the prior art, drawings required to be used in embodiments or technical solution in the prior art will be simply discussed. Apparently, the drawings described below are only some embodiments in the present application, and those of ordinary skill in the art can also obtain other drawings according to these drawings without creative efforts.

DESCRIPTION OF THE EMBODIMENTS

In view of the technical problems existing in the prior art, the inventor of the present application proposes the technical solution of the present application by virtue of long-term research and a large amount of practice and is mainly intended to provide a preparation method of a dual-function starch-based composite nanoparticles and application thereof in preparation of stable $W_1/O/W_2$ double-emulsion gel, so as to improve the oxidation resistance of unsaturated algae oil and the stability of double emulsion.

In the present application, the linear dextrin, which is prepared by carrying out limited hydrolysis on starch using α-amylase and pullulanase, grading via alcohol-alcohol gradient precipitation and adopting a 2,2,6,6-tetramethyl-1-piperidinyloxy free (hereinafter referred to as "TEMPO")-mediated directed-site quantitative oxidation technology has homogeneous polymerization degree and oxidation degree, and the composite nanoparticles with both oxidation resistance and interfacial stability are constructed due to high complexing action present between oxidized dextrin and curcumin and based on electrostatic interaction between oxidized dextrin and chitosan hydrochloride, and the double-emulsion gel is stabilized by this nanoparticles. In the present application, the method is simple and novel, the prepared double-emulsion gel has excellent oxidation resistance and stability, and the preparation process involved in the present application is simple, safe and pollution-free, and is easy to realize industrial production.

In summary, the design principle of the present application is mainly as follows: firstly, starch is subjected to limited hydrolysis using α-amylase and pullulanase and the alcohol-alcohol gradient precipitation method is adopted so as to prepare the linear dextrin with homogeneous molecular weight distribution, the C6 site of the linear dextrin undergoes directed-site quantitative oxidation based on a TEMPO/NaClO/NaBr oxidation system to obtain the oxidized dextrin with high anionic characteristics, and the oxidized dextrin-curcumin complex is prepared by further utilizing the complexing and embedding effect of the spiral cavity of dextrin on curcumin; oxidized dextrin-curcumin/chitosan hydrochloride composite nanoparticles are constructed based on electrostatic interaction between oxidized dextrin and chitosan hydrochloride. The composite nanoparticles dispersion liquid containing gel polysaccharide is used as an aqueous phase ($W_2$) to stabilize water in oil primary emulsion ($W_1$/O, where $W_1$ is mixed aqueous solution containing ethanol and NaCl, O is algae oil containing polyglycerol ricin ester (PGPR) or soybean lecithin) so as to prepare $W_1$/O/$W_2$ double emulsion with both oxidation resistance and interfacial stability, furthermore, the double emulsion with interfacial stability and gel network structure protecting effect is further obtained by a calcium ion induction method.

The technical solution, implementation process and principle will be further explained below.

One aspect of an embodiment of the present application provides a preparation method of a dual-function starch-based composite nanoparticles, comprising:

hydrolyzing starch to form starch hydrolyzate, thereby obtaining linear dextrin;

grading the linear dextrin by using an alcohol-alcohol gradient precipitation method to obtain linear dextrin having homogeneous molecular weight distribution;

oxidizing the linear dextrin by adopting a TEMPO/NaClO/NaBr oxidation system to obtain oxidized dextrin;

performing complex reaction on a first mixed system containing oxidized dextrin and curcumin to form an oxidized dextrin-curcumin complex; and forming an oxidized dextrin-curcumin/chitosan hydrochloride composite nanoparticles from the oxidized dextrin-curcumin complex and chitosan hydrochloride through electrostatic complexing action so as to obtain the dual-function starch-based composite nanoparticles.

In some embodiments, the preparation method comprises: hydrolyzing starch with α-amylase and pullulanase, and grading via alcohol-alcohol gradient precipitation to obtain linear dextrin with homogeneous molecular weight distribution. The present application takes renewable starch as a raw material to be deep processed, which can enlarge the application range of starch and meanwhile enriching the academic content of starch subject.

Further, the preparation method specifically comprises: heating and gelatinizing corn starch (high straight chain corn starch, common corn starch and waxy corn starch), adding α-amylase in the environment of acetate solution, hydrolyzing for 1-2 h at 50-60° C., heating to 100-110° C. to carry out enzyme deactivation for 10-20 min, then cooling to 50-60° C. and adding pullulanase to carry out de-branching treatment for 3~4 h, and finally carrying out enzyme deactivation on the obtained starch hydrolyzate (degree of hydrolysis is 18.2-25.3%), and then carrying out centrifugation, rotary evaporation and vacuum freeze drying to obtain the linear dextrin.

Further, the addition amount of α-amylase in each gram of corn starch is 2 U-6 U of enzyme unit, and the addition amount of pullulanase is 20 U-50 U of enzyme unit.

In some more preferred embodiments, the preparation method of the linear dextrin (LD) specifically comprises:

Corn starch milk having a mass fraction of 5 wt % is stirred for 1 h in boiling water bath so that the starch is completely gelatinized. Further, the gelatinized starch is put into acetate solution (0.02 mol/L, the pH value is 6) and α-amylase is added. The above mixture is hydrolyzed at 50-60° C. for 1-2 h, heated to 100° C. for enzyme deactivation and cooled to 50-60° C., pullulanase is added, de-branching treatment is carried out for 3-4 h, and the reaction liquid is placed in boiling water bath to be subjected to enzyme deactivation for 10-20 min after the reaction was ended. The reactants are centrifuged for 20 min at 4500 g, the precipitates are discarded, the supernatant is subjected to rotary evaporation, and the linear dextrin is obtained by vacuum freeze drying.

In some embodiments, the preparation method comprises: slowly adding ethanol to the linear dextrin dispersion liquid under continuous agitation so that the final concentration of ethanol is 10%-60%, then storing for 24-28 h at 4-6° C., and centrifuging to obtain the linear dextrin with homogeneous molecular weight distribution. In the present application, grading is carried out by alcohol-alcohol gradient precipitation to obtain the linear dextrin with homogeneous degree of polymerization. The method is simple and easily available. By adopting TEMPO directed-site quantitative oxidation, the spiral cavity of dextrin is retained, which is conducive to the complexation and embedding effect of dextrin on curcumin.

Further, the degree of polymerization (DP) of the linear dextrin is 20~68.

Further, the molecular weight range of the linear dextrin is 3.35~10.9 KDa.

In some more preferred embodiments, the grading method of the linear dextrin specifically comprises:

The linear dextrin (LD) is graded by using the alcohol-alcohol gradient precipitation method. In short, absolute ethanol is slowly added into LD dispersion liquid under the continuous stirring, so that the final concentrations of ethanol are respectively 10%, 20%, 30%, 40%, 50% and 60%, the above dispersion liquid is stored for 24 h at 4° C. and then centrifuged at 4500 g to obtain precipitate components which are named LD-10, LD-20, LD-30, LD-40, LD-50 and LD-60.

In some embodiments, the preparation method specifically comprises:

providing a mixed solution containing 2,2,6,6-tetramethyl-1-piperidinyloxy free radical (TEMPO), sodium bromide (NaBr) and water; and mixing the mixed solution with the linear dextrin, adjusting the pH value of the obtained second mixed system to 10~10.75, then adding NaClO and keeping the pH value of the second mixed system unchanged, and precipitating out the obtained oxidized dextrin when the oxidization degree of the linear dextrin is 30~90%.

Preferably, the molar ratio of the glucose unit to TEMPO in the linear dextrin is 1:(0.01~0.02), namely, the addition amount of TEMPO is that 0.01-0.02 mol of TEMPO is added in the glucose unit of the linear dextrin per mol.

Further, the molar ratio of the glucose unit to NaBr in the linear dextrin is 1:(0.1~0.3), namely, the addition amount of NaBr is that 0.1-0.3 mol of NaBr is added in the glucose unit of the linear dextrin per mol.

Further, the oxidization of the oxidized dextrin only occurs at the C6 site of hydroxyl of dextrin.

Further, the mass ratio of the linear dextrin to NaClO is (25~70):100.

Further, the oxidization degree of the oxidized dextrin is 30%~90%.

In some more preferred embodiments, the preparation method of the oxidized dextrin specifically comprises:

5 wt % dextrin solution is placed into 5° C. ice water bath, and 2,2,6,6-tetramethyl-1-piperidinyloxy free radical (TEMPO) and sodium bromide are dissolved in 100 ml of distilled water. After TEMPO is completely dissolved, the solution is added to 5° C. dextrin solution, and the pH value of the solution is adjusted to 10.75 with 0.5 mol/L NaOH. A certain amount of NaClO is added to dextrin solution, and the pH of the solution is kept unchanged by using a pH-stat method. When a proper oxidation degree is reached, 75% ethanol is added to precipitate the needed products. The sample is washed repeatedly by using the mixed solution of water and acetone until $Cl^-$ is not detected in the supernatant. The precipitate is washed with acetone and then dried in a 45° C. oven.

In some embodiments, the preparation method specifically comprises:

providing ethanol solution containing curcumin;

providing water dispersion containing the oxidized dextrin and heating for 30-45 min at 90-100° C., and then cooling to 65-80° C.;

uniformly mixing the ethanol solution containing curcumin with the water dispersion containing the oxidized dextrin to form the first mixed system, carrying out complex reaction for 2-4 h at 65-80° C. to obtain the oxidized dextrin-curcumin complex.

Further, the concentration of curcumin in the ethanol solution containing curcumin is 4-6 mg/mL.

Further, the concentration of the oxidized dextrin in the water dispersion containing the oxidized dextrin is 8-12 mg/mL.

Further, the loading amount of curcumin in the oxidized dextrin-curcumin complex is 12 μg/mg~35 μg/Mg, and the complexation rate is 8%~25%.

In some more preferred embodiments, the preparation method of the oxidized dextrin-curcumin complex specifically comprises:

The oxidized dextrin-curcumin complex is prepared by using a co-precipitation method. The curcumin is dissolved into anhydrous ethanol (4 mg/mL) as the original solution; oxidized dextrin is dispersed into distilled water until the final concentration is 10 mg/mL. The resulting dispersion is heated for 30 min at 100° C., and then cooled to 80° C. Different volumes of curcumin are added into oxidized dextrin solution and mildly stirred for 2 h at 80° C. The mixture is stored for 12 h at 4° C. and centrifuged for 15 min at 10000 g to obtain precipitate, and the precipitate is washed three times with 50% anhydrous ethanol, and dried in the 40° C. oven.

Further, the volumes of curcumin added into the oxidized dextrin solution are 1.5 ml, 2.0 ml, 3.0 ml, 6 ml, 9 ml and 12 ml respectively.

In some embodiments, the preparation method specifically comprises: in a reaction system of 20~25° C. and pH of 4~4.5, the oxidized dextrin-curcumin complex is uniformly mixed with chitosan hydrochloride for 30-45 min in a mass ratio of (1:5)~(5:1), and the oxidized dextrin-curcumin/chitosan hydrochloride composite nanoparticles are formed through electrostatic complexing action. In the present application, the composite nanoparticles are prepared by using the electrostatic interaction method. The reaction conditions are mild and the method is simple. The obtained nanoparticles have suitable wettability, spherical shape, good emulsification and interface stability.

In some more preferred embodiments, the preparation method of the oxidized dextrin-curcumin/chitosan hydrochloride composite nanoparticles specifically comprises:

The oxidation dextrin-curcumin complex is dissolved into distilled water and stirred at 800 RPM until the complex is completely dissolved to obtain 0.5 wt % oxidized dextrin-curcumin solution; chitosan hydrochloride is dissolved into distilled water to obtain 1.5 wt % chitosan hydrochloride solution; the pH value of the solution is adjusted with 0.5 mol/L HCl, and the oxidized dextrin-curcumin solution is further added into the chitosan hydrochloride solution to be mixed and stirred for 30 min so as to promote the formation of composite nanoparticles. And the obtained oxidized dextrin-curcumin/chitosan hydrochloride composite nanoparticles are freeze-dried for further analysis.

Further, the pH value of the mixed solution of the oxidized dextrin-curcumin solution and chitosan hydrochloride solution is 4~4.5.

Further, the mass ratio of the oxidized dextrin-curcumin complex to chitosan hydrochloride can be 5:1, 3:1, 2:1, 1:1, 1:2, 1:3, 1:5 and the like.

Another aspect of an embodiment of the present application also provides a dual-function starch-based composite nanoparticles prepared by using the above method.

Further, the dual-function starch-based composite nanoparticles have a particle size of 285.3 nm~848.6 nm, a spherical shape, homogeneous spherical shape distribution, good oxidation resistance and emulsification performance.

Another aspect of an embodiment of the present application also provides a preparation method of double-emulsion gel (namely, $W_1/O/W_2$ double-emulsion gel stabilized by oxidized dextrin-curcumin/chitosan hydrochloride composite nanoparticles), comprising:

preparing the dual-function starch-based composite nanoparticles according to the above method;

uniformly mixing chlorides such as sodium chloride or potassium chloride or magnesium chloride, gelatin or ethanol or glucose with water to form the first aqueous phase solution, and uniformly mixing the first aqueous phase solution with the oil phase components to form primary emulsion;

uniformly mixing the second aqueous solution containing the dual-function starch-based composite nanoparticles with the primary emulsion by using high pressure homogenization and microfluidization technologies to obtain double emulsion containing gel polysaccharides; and treating the double emulsion containing gel polysaccharide for 1 h in 80° C. water bath, and adding 0.5 mmol/L $Ca^{2+}$ to induce cross-linking reaction of gel polysaccharide, and cooling to 30~35° C. to obtain double-emulsion gel having good stability.

In some embodiments, the preparation method specifically comprises:

shearing the mixed solution of the primary emulsion and the second aqueous phase solution by using the high pressure homogenizing technology to form crude double emulsion, then further homogenizing the crude double emulsion for 3~5 times under the 103.4~121 MPa by using the high-pressure microfluidization technology to obtain the $W_1/O/W_2$ double emulsion, and treating the double emulsion containing gel polysaccharide for 1 h in the 80° C. water bath, and the 0.5 mmol/L $Ca^{2+}$ to induce cross-linking reaction of gel polysaccharide, and cooling to 30-35° C. to obtain double-emulsion gel having good stability.

In some preferred embodiments, the preparation method of the $W_1/O/W_2$ double-emulsion gel specifically comprises the following steps:

a) Preparation of $W_1/O$ Emulsion

PGPR is added to algae oil, heated and stirred for 20 min at 60° C. so that PGPR is completely dissolved to prepare an oil phase (O), 0.1M NaCl and 20% ethanol are dissolved into distilled water to prepare an aqueous phase ($W_1$), and $W_1$ is dropwise added to the oil phase and stirred for 30 min under 800 rpm to prepare $W_1$/O crude emulsion; and the crude emulsion is sheared for 20 min under 20000 rpm to obtain $W_1$/O fine emulsion.

b) Preparation of $W_1$/O/$W_2$ Double-Emulsion Gel $W_1$/O/$W_2$ double-emulsion gel is prepared by dispersing the primary emulsion $W_1$/O to the aqueous phase $W_2$ in different volume ratios. $W_2$ is dispersion liquid containing different concentrations of gel polysaccharide and oxidized dextrin-curcumin/chitosan hydrochloride composite nanoparticles. After being mixed, they are treated by high pressure microfluidization to obtain $W_1$/O/$W_2$ double emulsion. The double emulsion containing gel polysaccharide is treated for 1 h in 80° C. water bath, 0.5 mmol/L $Ca^{2+}$ is added, and double-emulsion gel having good stability is obtained when cooling to 30-35° C.

Further, in the preparation of $W_1$/O/$W_2$ double emulsion, the volume ratio of the $W_1$/O primary emulsion to the second aqueous phase solution (namely aqueous phase $W_2$) is (1:9)~(5:5).

Further, the concentration of the dual-function starch-based composite nanoparticles in the second aqueous phase solution (namely aqueous phase $W_2$) is 0.5 wt %~3 wt %.

Further, the gel polysaccharide in the double emulsion containing gel polysaccharide is any one of gellan gum, konjac glucomannan, sodium alginate, pectin and the like or a combination of more than two thereof, but not limited thereto.

Further, the concentration of the gel polysaccharide in the double emulsion containing gel polysaccharide is 2~8 wt %.

Further, in the preparation of $W_1$/O emulsion, the volume ratio of the oil phase component to the first aqueous phase solution (namely aqueous phase $W_1$) is (2:8)~(5:5).

Further, the preparation method of $W_1$/O emulsion comprises: dissolving polyglycerol ricinol ester or soybean lecithin into an oil phase solvent and heating and stirring for 10~20 min at 55~60° C. so as to prepare the oil phase component.

Further, the oil phase solvent comprises algae oil, but is not limited thereto.

Further, the mass ratio of PGPR or soybean lecithin to oil phase solvent is (3~6):100, that is to say, the addition amount of PGPR is 3 wt %-6 wt % of that of algae oil.

Where, as one of more preferred embodiments of the present application, the preparation method of the $W_1$/O/$W_2$ double-emulsion gel more specifically comprises the following steps:

1) Preparation of Linear Dextrin (LD)

Corn starch having mass fraction of 5 wt % is placed in boiling water bath to be stirred for 1 h so that the starch is completely gelatinized, the gelatinized starch is further put in acetate solution (0.02 mol/L, pH is 6), α-amylase is added, hydrolysis is carried out for 1-2 h at 50-60° C., the temperature is raised to 100° C. for enzyme deactivation and then reduced to 50-60° C., pullulanase is added to carry out de-branching treatment for 3-4 h, and after the reaction is ended, reaction liquid is placed into the boiling water bath to carry out enzyme deactivation for 10 min. The reactant is centrifuged for 20 min at 4500 g, the precipitate is discarded, rotary evaporation is carried out on supernatant, and linear dextrin is obtained by vacuum freeze drying.

2) Grading of Linear Dextrin

LD is graded by using the alcohol-alcohol gradient precipitation method. In short, anhydrous ethanol is slowly added into LD dispersion liquid under continuous agitation, so that the final concentrations of ethanol are 10%, 20%, 30%, 40%, 50%, 60% respectively. The obtained products are stored for 24 h at 4° C. and centrifuged at 4500 g to obtain precipitate component which are named LD-10, LD-20, LD-30, LD-40, LD-50 and LD-60.

3) Preparation of Oxidized Dextrin 5 wt % dextrin solution is placed in 5° C. ice water bath, and 2,2,6,6-tetramethyl-1-piperidinyloxy free radical (TEMPO) and sodium bromide are dissolved into 100 ml of distilled water. After TEMPO is completely dissolved, the solution is added to 5° C. dextrin solution, and the pH value of the solution is adjusted to 10.75 with 0.5 mol/L NaOH. A certain amount of NaClO is added to dextrin solution, and the pH value of solution is kept unchanged by the pH-stat method. When the proper oxidation degree is reached, 75% ethanol is added to precipitate the needed products. The sample is washed repeatedly by using the mixed solution of water and acetone until $Cl^-$ is not detected in the supernatant. The obtained precipitates are washed with acetone and then dried in a 45° C. oven.

4) Preparation of Oxidation Dextrin-Curcumin Complex

The oxidation dextrin-curcumin complex is prepared by the co-precipitation method. Curcumin is dissolved into anhydrous ethanol (4 mg/mL) as the original solution; oxidized dextrin is dispersed into distilled water until the final concentration is 10 mg/mL. The resulting dispersion liquid is heated for 30 min at 100° C., and then cooled to 80° C. Different volumes of curcumin are added into the oxidized dextrin solution, and mildly stirred for 2 h at 80° C. The mixture is kept for 12 h at 4° C. and centrifuged for 15 min at 10000 g to obtain the precipitate, and the precipitate is washed three times with 50% anhydrous ethanol, and then dried in a 40° C. oven.

5) Preparation of Oxidized Dextrin-Curcumin/Chitosan Hydrochloride Composite Nanoparticles The oxidized dextrin-curcumin complex is dissolved into distilled water, and stirred at 800 rpm until the oxidized dextrin-curcumin complex is completely dissolved to obtain 0.5 wt % oxidized dextrin-curcumin solution; chitosan hydrochloride is dissolved into distilled water to obtain 1.5 wt % chitosan hydrochloride solution; the pH values of the two solutions are adjusted with 0.5 mol/L HCl, and then the oxidized dextrin-curcumin solution is dropwise added into the chitosan hydrochloride solution, both are mixed and stirred for 30 min to promote the formation of composite nanoparticles. And the oxidized dextrin-curcumin/chitosan hydrochloride composite nanoparticles are freeze-dried for further analysis.

Application of the oxidized dextrin-curcumin/chitosan hydrochloride composite nanoparticles prepared in the present application is to replace the surfactant of the $W_2$ phase of the double-emulsion gel so as to improve the stability of the double-emulsion gel, specifically comprising the following steps:

a) Preparation of $W_1$/O Emulsion

The PGPR is added to algae oil, and heated and stirred for 20 min at 60° C. so that PGPR is completely dissolved to prepare an oil phase (O). 0.1 mol/L NaCl and 20% ethanol are dissolved into distilled water to prepare an aqueous phase ($W_1$), and then $W_1$/O crude emulsion is prepared by dropwise adding $W_1$ into the oil phase and stirring for 30 min at 800 rpm; the obtained crude emulsion is sheared for 10 min at 20000 rpm to obtain $W_1$/O fine emulsion.

b) Preparation of $W_1$/O/$W_2$ Double-Emulsion Gel

The $W_1$/O/$W_2$ double-emulsion gel is prepared by dispersing primary emulsion $W_1$/O into a $W_2$ aqueous phase in different volume ratios. $W_2$ is dispersion liquid containing different concentrations of gel polysaccharide and oxidized dextrin-curcumin/chitosan hydrochloride composite nanoparticles. After they are mixed, the $W_1/O/W_2$ double emulsion is obtained by high pressure microfluidization treatment. The double emulsion containing gel polysaccharide is placed in 80° C. water bath to be treated for 1 h, 0.5 mmol/L $Ca^{2+}$ is added, and the above double emulsion is cooled to 30-35° C. to obtain double-emulsion gel having good stability.

Another aspect of an embodiment of the present application also provides the double-emulsion gel prepared by using the above method.

Further, the double emulsion is 25.96~73.33 μm in droplet size, and has good storage stability and excellent antioxidant activity.

Further, the double-emulsion gel has good viscoelasticity, self-supporting characteristics and a dense three-dimensional network structure.

In the present application, the composite nanoparticles are used for preparation of the double-emulsion gel. The emulsion is stabilized by an interfacial layer formed from particles and a gel network. The emulsion has higher stability, good oxidation resistance and long-term storage stability (180 days), as compared with the emulsion stabilized by the surfactant.

Another aspect of an embodiment of the present application also provides use of the above-mentioned double-emulsion gel in the fields of nutrient protection, drug delivery or cosmetic preparation.

The molecular weight of the graded dextrin is measured by HPSEC-MALLS-RI; the particle size and potential of the composite nanoparticles are determined by a zeta potential analyzer, and the wettability of the composite nanoparticles is evaluated; the contents of hydroperoxide and malonaldehyde are determined by an iron thiocyanate method and a thiobarbituric acid method, and the oxidation resistance of the double emulsion is evaluated; and change in the particle size of the emulsion in the process of storage is determined by using a laser particle size analyzer, and the stability of the double emulsion is evaluated. In the present application, the double-emulsion gel stabilized by the composite nanoparticles has good oxidation resistance and interface stability.

In summary, the electrostatic interaction method is used to prepare composite nanoparticles in the present application. The reaction conditions are mild and the method is simple. The nanoparticles obtained has appropriate wettability, spherical shape, good emulsification and interface stability. In the present application, the composite nanoparticles are used to prepare the double-emulsion gel. The emulsion is stabilized by an interfacial layer formed from particles and a gel network. The emulsion has higher stability, good oxidation resistance and long-term storage stability as compared with the emulsion stabilized by the surfactant (180 days). In the present application, the double-emulsion gel is mild in reaction conditions, simple in preparation method and easy to produce on large scale, and can be applied to the fields of nutrition protection, drug delivery, cosmetic preparation and the like.

The technical solution of the present application will be further described in detail through several embodiments and accompanying drawings. However, the selected embodiments are only for explaining the present application but not limiting the scope of the present application.

Example 1

1) Preparation of Linear Dextrin (LD)

20 g of ordinary corn starch was prepared into 5 wt % starch emulsion, and the 5 wt % starch emulsion was stirred for 1 h in boiling water bath so that starch was completely gelatinized. Further, the gelatinized starch was further placed in acetate solution (0.02 mol/L, pH is 6), 80 U of α-amylase was added and hydrolyzed for 1.5 h at 60° C., the temperature was raised to 100° C. for enzyme deactivation, 1000 U of pullulanase was added after cooling to 55° C. to carry out de-branching for 3 h. After the reaction was ended, the reaction solution was placed in boiling water bath to carry out enzyme deactivation for 10 minutes. The reactants were centrifuged for 20 min at 4500 g, the precipitates were discarded, the supernatant was rotary evaporated, and the linear dextrin was obtained by vacuum freeze drying.

2) Grading of Linear Dextrin

LD was graded by using the alcohol-alcohol gradient precipitation method. In short, anhydrous ethanol was slowly added into LD dispersion liquid under continuous agitation, so that the final concentrations of ethanol were 10%, 20%, 30%, 40%, 50%, 60% respectively. The above dispersion liquids were stored for 24 h at 4° C. and centrifuged at 4500 g to obtain the precipitate components which are named LD-10, LD-20, LD-30, LD-40, LD-50 and LD-60.

3) Preparation of Oxidized Dextrin 5 wt % dextrin solution was put into 5° C. ice water bath, and 0.048 g of 2,2,6,6-tetramethyl-1-piperidinyloxy free radical (TEMPO) and 0.635 g of sodium bromide were dissolved into 100 mL of distilled water. After TEMPO was completely dissolved, the solution was added to 5° C. dextrin solution, and the pH value of the solution was adjusted to 10.75 with 0.5 mol/L NaOH. 50 wt % NaClO was added to dextrin solution, and the pH value of the solution was kept unchanged by using the pH-stat method. When the oxidation degree of the $C_6$ site of dextrin was 70%, 75% ethanol was added to precipitate the required products. The sample was washed repeatedly by using the mixed solution of water and acetone until $Cl^-$ was not detected in the supernatant. The precipitate was washed with acetone and dried in an oven at 45° C.

4) Preparation of Oxidation Dextrin-Curcumin Complex

The oxidation dextrin-curcumin complex was prepared by using the co-precipitation method. The curcumin was dissolved into anhydrous ethanol (6 mg/ml) as the original solution; oxidized dextrin was dispersed into distilled water until the final concentration is 8 mg/mL. The resulting dispersion liquid was heated for 40 min at 95° C. and then cooled to 70° C. 1.5 ml of curcumin was added to the dextrin solution and stirred for 3 h at 65° C. The mixture was stored for 3 h at 4° C. and centrifuged for 15 min at 10000 g to obtain the precipitate, and the obtained precipitate was washed three times with 50% anhydrous ethanol, and dried in a 40° C. oven.

5) Preparation of Oxidized Dextrin-Curcumin/Chitosan Hydrochloride Composite Nanoparticles The oxidized dextrin-curcumin complex was dissolved into distilled water and stirred at 800 rpm at 25° C. until the oxidized dextrin-curcumin complex was completely dissolved to obtain 0.5 wt % oxidized dextrin-curcumin solution; chitosan hydrochloride was dissolved into distilled water to obtain 1.5 wt % chitosan hydrochloride solution; the pH values of two solutions were adjusted to 4.5 with 0.5 mol/L HCl, and then the oxidized dextrin-curcumin solution was further dropwise added into chitosan hydrochloride solution, the mass ratio of the both is 5:1, they were mixed and stirred for 30 min to promote the formation of composite nanoparticles. And, the oxidized dextrin-curcumin/chitosan hydrochloride composite nanoparticles were freeze-dried for further analysis.

6) Preparation of $W_1/O/W_2$ Double-Emulsion Gel Stabilized by Oxidized Dextrin-Curcumin/Chitosan Hydrochloride Composite Nanoparticles.

a) Preparation of $W_1/O$ Emulsion

The 4 wt % PGPR was added to algae oil, and heated and stirred for 10 min at 60° C. so that PGPR was completely dissolved to prepare an oil phase (O). 0.1 mol/L NaCl and 20% ethanol were dissolved into the distilled water to prepare an aqueous phase ($W_1$). The $W_1$ was dropwise added to the oil phase, and the volume ratio of the two was 2:8 (O:$W_1$), the above oil phase was stirred for 30 min at 800 rpm so as to prepare $W_1/O$ crude emulsion; the obtained crude emulsion was sheared for 10 min at 20000 rpm to obtain $W_1/O$ fine emulsion.

b) Preparation of ($W_1/O/W_2$) Double-Emulsion Gel $W_1/O/W_2$ double-emulsion gel was prepared by dispersing primary emulsion $W_1/O$ to the $W_2$ aqueous phase in different volume ratios, and the volume ratio of the two was 4:6 ($W_1/O:W_2$). $W_2$ is dispersion liquid containing 1.5 wt % oxidized dextrin-curcumin/chitosan hydrochloride composite nanoparticles and 2 wt % sodium alginate. After mixing, 103.4 MPa microfluidization treatment was carried out four times to obtain the $W_1/O/W_2$ double emulsion. The double emulsion containing sodium alginate was treated for 1 h in the 80° C. water bath, 0.5 mmol/L $Ca^{2+}$ was added and cooled to 32° C. to obtain double-emulsion gel having good stability.

Example 2

1) Preparation of Linear Dextrin (LD)

20 g of ordinary corn starch was prepared into 5 wt % starch emulsion, and stirred for 1 h in boiling water bath so that starch was completely gelatinized. Further, the gelatinized starch was further placed in acetate solution (0.02 mol/L, pH is 6), 40 U of α-amylase was added and hydrolyzed for 2 h at 50° C., the temperature was raised to 110° C. for enzyme deactivation, 600 U of pullulanase was added after cooling to 60° C. to carry out de-branching for 3.5 h, After the reaction was ended, the reaction solution was placed in a boiling water bath to carry out enzyme deactivation for 15 min. The reactants were centrifuged for 20 min at 4500 g, the precipitates were discarded, the supernatant was rotary evaporated, and the linear dextrin was obtained by vacuum freeze drying.

2) Grading of Linear Dextrin

LD was graded by using the alcohol-alcohol gradient precipitation method. In short, anhydrous ethanol was slowly added into LD dispersion liquid under continuous agitation, so that the final concentrations of ethanol were 10%, 20%, 30%, 40%, 50%, 60% respectively. The above dispersion liquids were stored for 28 h at 6° C. and centrifuged at 4500 g to obtain the precipitate components which were named LD-10, LD-20, LD-30, LD-40, LD-50 and LD-60.

3) Preparation of Oxidized Dextrin 5 wt % dextrin solution was put into 5° C. ice water bath, and 0.096 g of 2,2,6,6-tetramethyl-1-piperidinyloxy free radical (tempo) and 0.3175 g of sodium bromide were dissolved into 100 mL of distilled water. After TEMPO was completely dissolved, the solution was added to 5° C. dextrin solution, and the pH value of the solution was adjusted to 10.5 with 0.5 mol/L NaOH. 35 wt % NaClO was added to dextrin solution, and the pH value of the solution was kept unchanged by using the pH-stat method. When the oxidation degree of the $C_6$ site of dextrin was 40%, 75% ethanol was added to precipitate the required products. The sample was washed repeatedly by using the mixed solution of water and acetone until $Cl^-$ was not detected in the supernatant. The precipitate was washed with acetone and dried in an oven at 45° C.

4) Preparation of Oxidation Dextrin-Curcumin Complex

The oxidation dextrin-curcumin complex was prepared by using the co-precipitation. Curcumin was dissolved into anhydrous ethanol (4 mg/ml) as the original solution; oxidized dextrin was dispersed into distilled water until the final concentration is 10 mg/mL. The resulting dispersion liquid was heated for 30 min at 100° C. and then cooled to 70° C. 12 mL of curcumin was added to the dextrin solution and stirred for 2 h at 70° C. The mixture was stored for 12 h at 4° C. and centrifuged for 15 min at 10000 g to obtain the precipitate, and the obtained precipitate was washed three times with 50% anhydrous ethanol, and dried in a 40° C. oven.

5) Preparation of Oxidized Dextrin-Curcumin/Chitosan Hydrochloride Composite Nanoparticles The oxidized dextrin-curcumin complex was dissolved into distilled water and stirred at 800 rpm at 20° C. until the oxidized dextrin-curcumin complex was completely dissolved to obtain 0.5 wt % oxidized dextrin curcumin solution; chitosan hydrochloride was dissolved into distilled water to obtain 1.5 wt % chitosan hydrochloride solution; the pH values of two solutions were adjusted to 4.25 with 0.5 mol/L HCl, and then the oxidized dextrin-curcumin solution was further dropwise added into chitosan hydrochloride solution, the mass ratio of the two is 1:1, and they were mixed and stirred for 45 min to promote the formation of composite nanoparticles. And, the oxidized dextrin-curcumin/chitosan hydrochloride composite nanoparticles were freeze-dried for further analysis.

6) Preparation of $W_1/O/W_2$ Double-Emulsion Gel Stabilized by Oxidized Dextrin-Curcumin/Chitosan Hydrochloride Composite Nanoparticles.

a) Preparation of $W_1/O$ Emulsion 6 wt % soy bean lecithin was added to algae oil, and heated and stirred for 20 min at 55° C. so that the soy bean lecithin was completely dissolved to prepare an oil phase (O). 0.1 mol/L KCl and 20% ethanol were dissolved into the distilled water to prepare an aqueous phase ($W_1$). The $W_1$ was dropwise added to the oil phase, and the volume ratio of the two was 4:6 (O:$W_1$), and the above oil phase was stirred for 30 min at 800 rpm so as to prepare $W_1/O$ crude emulsion; the obtained crude emulsion was sheared for 10 min at 20000 rpm to obtain $W_1/O$ fine emulsion.

b) Preparation of ($W_1/O/W_2$) Double-Emulsion Gel $W_1/O/W_2$ double-emulsion gel was prepared by dispersing primary emulsion $W_1/O$ to the $W_2$ aqueous phase in different volume ratios, and the volume ratio of the two was 1:9 ($W_1/O:W_2$). $W_2$ is dispersion liquid containing 3 wt % oxidized dextrin-curcumin/chitosan hydrochloride composite nanoparticles and 5 wt % konjac glumcomannan. After mixing, 121 MPa microfluidization treatment was carried out three times to obtain the $W_1/O/W_2$ double emulsion. The double emulsion containing konjac glumcomannan was treated for 1 h in the 80° C. water bath, 0.5 mmol/L $Ca^{2+}$ was added and the double-emulsion gel having good stability was obtained when cooling to 32° C.

Example 3

1) Preparation of Linear Dextrin (LD)

20 g of high-linear-chain corn starch was prepared into 5 wt % starch emulsion, and stirred for 1 h in boiling water bath so that starch was completely gelatinized. Further, the gelatinized starch was further placed in acetate solution (0.02 mol/L, pH is 6), 120 U of α-amylase was added and hydrolyzed for 1 h at 55° C., the temperature was raised to 105° C. for enzyme deactivation, 400 U of pullulanase was added after cooling to 50° C. to carry out de-branching for 4 h. After the reaction was ended, the reaction solution was placed in boiling water bath to carry out enzyme deactivation for 20 min. The reactants were centrifuged for 20 min at 4500 g, the precipitates were discarded, the supernatant was spin evaporated, and the linear dextrin was obtained by vacuum freeze drying.

2) Grading of Linear Dextrin

LD was graded by using the alcohol-alcohol gradient precipitation method. In short, anhydrous ethanol was slowly added into LD dispersion under continuous agitation, so that the final concentrations of ethanol were 10%, 20%, 30%, 40%, 50%, 60% respectively. The above dispersion liquids were stored for 26 h at 5° C. and centrifuged at 4500 g to obtain the precipitate components which are named LD-10, LD-20, LD-30, LD-40, LD-50 and LD-60.

3) Preparation of Oxidized Dextrin 5 wt % dextrin solution was put into 5° C. ice water bath, and 0.072 g of 2,2,6,6-tetramethyl-1-piperidinyloxy free radical (tempo) and 0.9525 g of sodium bromide were dissolved into 100 mL of distilled water. After TEMPO was completely dissolved, the solution was added to 5° C. dextrin solution, and the pH value of the solution was adjusted to 10 with 0.5 mol/L NaOH. 70 wt % NaClO was added to dextrin solution, and the pH value of the solution was kept unchanged by using the pH-stat method. When the oxidation degree of the $C_6$ site of dextrin was 90%, 75% ethanol was added to precipitate the required products. The sample was washed repeatedly by using the mixed solution of water and acetone until $Cl^-$ was not detected in the supernatant. The precipitate was washed with acetone and dried in a 45° C. oven.

4) Preparation of Oxidation Dextrin-Curcumin Complex

The oxidation dextrin-curcumin complex was prepared by using the co-precipitation. Curcumin was dissolved into anhydrous ethanol (5 mg/ml) as the original solution; oxidized dextrin was dispersed into distilled water until the final concentration is 12 mg/mL. The resulting dispersion liquid was heated at 90° C. for 45 min and then cooled to 65° C. 6 ml of curcumin was added to the dextrin solution and stirred at 80° C. for 4 h. The mixture was stored for 12 h at 4° C. and centrifuged for 15 min at 10000 g to obtain the precipitate, and the obtained precipitate was washed three times with 50% anhydrous ethanol and dried in a 40° C. oven.

5) Preparation of Oxidized Dextrin-Curcumin/Chitosan Hydrochloride Composite Nanoparticles The oxidized dextrin-curcumin complex was dissolved into distilled water and stirred at 800 rpm at 23° C. until the oxidized dextrin-curcumin complex was completely dissolved to obtain 0.5 wt % oxidized dextrin curcumin solution; chitosan hydrochloride was dissolved into distilled water to obtain 1.5 wt % chitosan hydrochloride solution; the pH values of two solutions were adjusted to 4 with 0.5 mol/L HCl, and then the oxidized dextrin-curcumin solution was further dropwise added into chitosan hydrochloride solution, the mass ratio of the two is 1:5, they were mixed and stirred for 35 min to promote the formation of composite nanoparticles. And, the oxidized dextrin-curcumin/chitosan hydrochloride composite nanoparticles were freeze-dried for further analysis.

6) Preparation of $W_1/O/W_2$ Double-Emulsion Gel Stabilized by Oxidized Dextrin-Curcumin/Chitosan Hydrochloride Composite Nanoparticles.

a) Preparation of $W_1/O$ Emulsion

The 5 wt % PGPR was added to algae oil, and heated and stirred for 15 min at 58° C. so that PGPR was completely dissolved to prepare an oil phase (O). 0.1 mol/L $MgCl_2$ and 20% glucose were dissolved into the distilled water to prepare an aqueous phase ($W_1$). The $W_1$ was dropwise added to the oil phase, and the volume ratio of the two was 5:5 ($O:W_1$), the above oil phase was stirred for 30 min at 800 rpm so as to prepare $W_1/O$ crude emulsion; the obtained crude emulsion was sheared for 10 min at 20000 rpm to obtain $W_1/O$ fine emulsion.

b) Preparation of ($W_1/O/W_2$) Double-Emulsion Gel $W_1/O/W_2$ double-emulsion gel was prepared by dispersing primary emulsion $W_1/O$ to the $W_2$ aqueous phase in different volume ratios, and the volume ratio of the two was 5:5 ($W_1/O:W_2$). $W_2$ is dispersion liquid containing 0.5 wt % oxidized dextrin-curcumin/chitosan hydrochloride composite nanoparticles and 8 wt % konjac glumcomannan. After mixing, 112 MPa microfluidization treatment was carried out five times to obtain the $W_1/O/W_2$ double emulsion. The double emulsion containing gellan gum was treated for 1 h in the 80° C. water bath, 0.5 mmol/L $Ca^{2+}$ was added and cooled to 35° C. to obtain double-emulsion gel having good stability.

The inventor of the present application also performs performance characterization and test on the products obtained by the above examples.

Figure 1A:
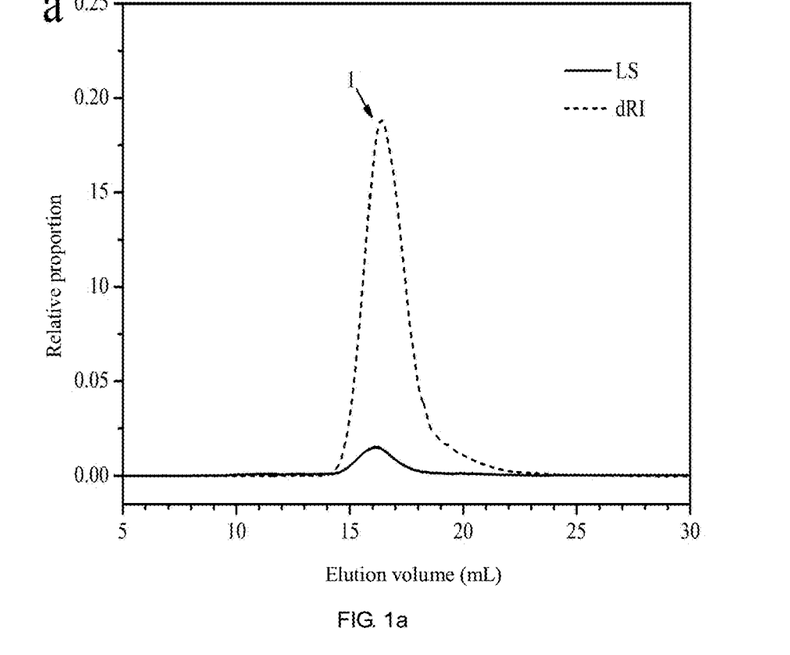
FIGS. 1a-1c are HPSEC-MALLS-RI spectrums of graded dextrin according to a typical embodiment of the present application respectively.
Figure 1B:
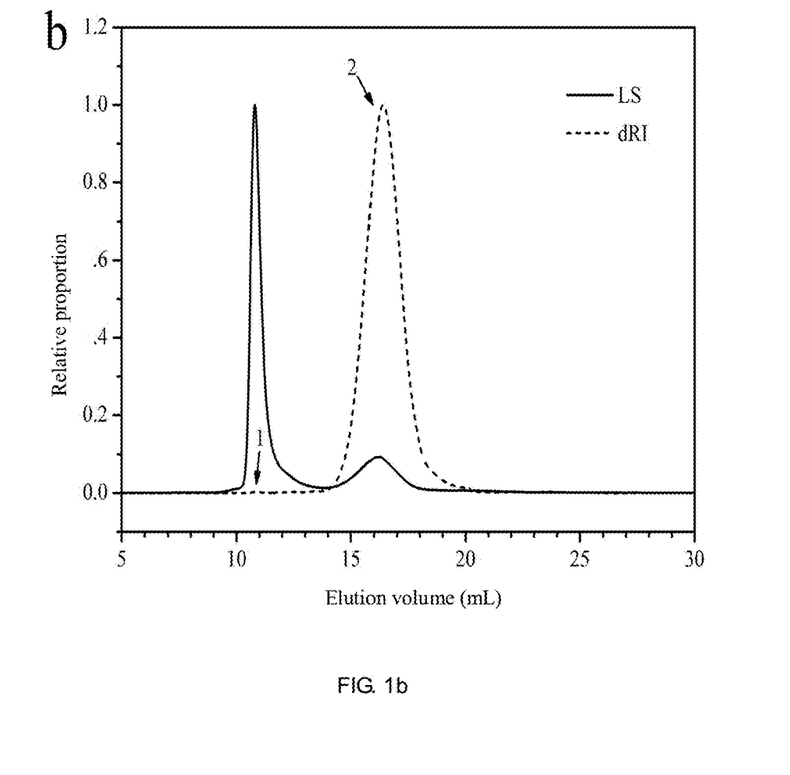
Figure 1C:
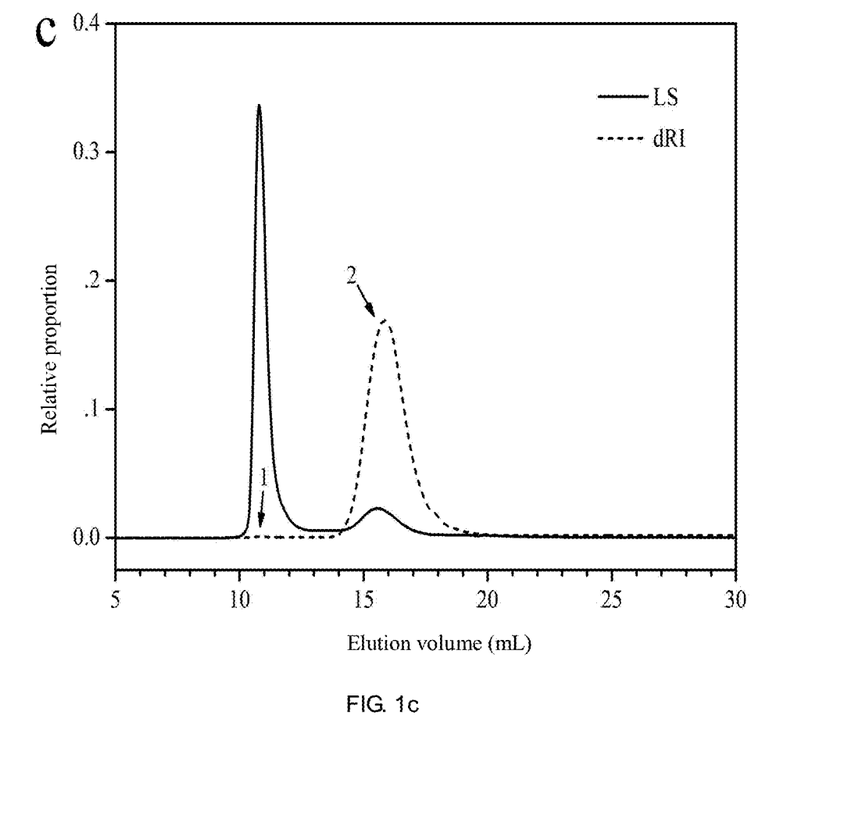

Referring to FIG. 1a-FIG. 1c, FIG. 1a-FIG. 1c are HPSEC-MARS-RI spectrums of graded dextrin components, in which FIG. 1a, FIG. 1b and FIG. 1c respectively represent LD-60, LD-40 and LD-10. From FIG. 1a to FIG. 1c, it can be seen that the dextrin obtained by alcohol-alcohol gradient precipitation has a homogeneous molecular weight distribution.

Figure 2:
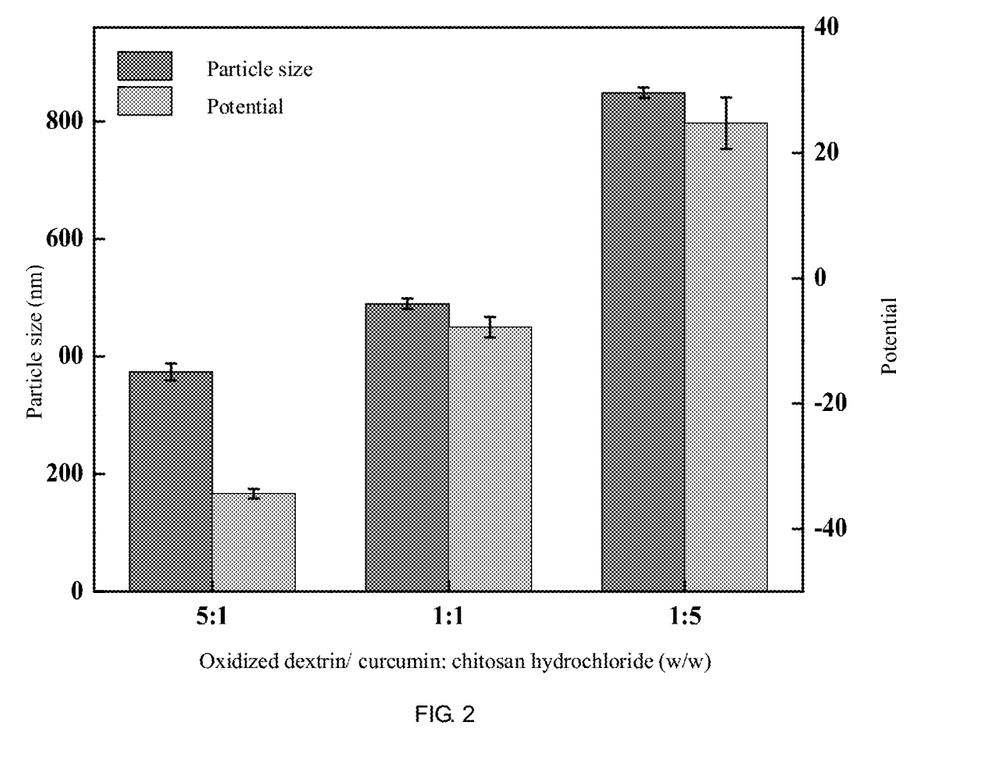
FIG. 2 is a diagram of particle sizes and potentials of composite nanoparticles in different proportions according to a typical embodiment of the disclosure.

FIG. 2 is a diagram of particle sizes and potentials of composite nanoparticles in different ratios in the above embodiment. It can be seen from FIG. 2 that the ratio of oxidized dextrin-curcumin complex to chitosan hydrochloride is 5:1, and the smallest composite nanoparticles are formed, which have particle size of 374.2 nm and absolute potential value of 34.25 mV, indicating that the composite nanoparticles have good stability.

Figure 3A:
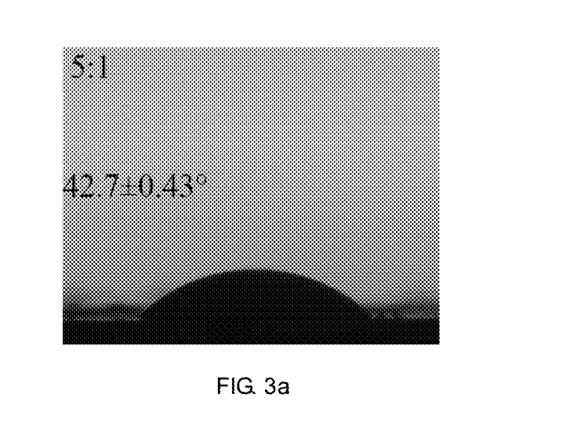
FIGS. 3a-3c are diagrams of contact angles of composite nanoparticles in different proportions according to a typical embodiment of the present application respectively.
Figure 3B:
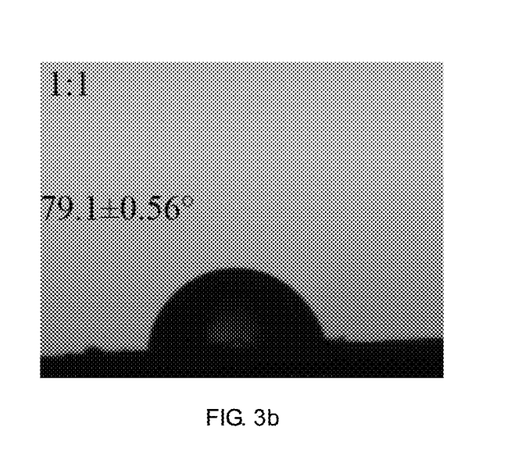
Figure 3C:
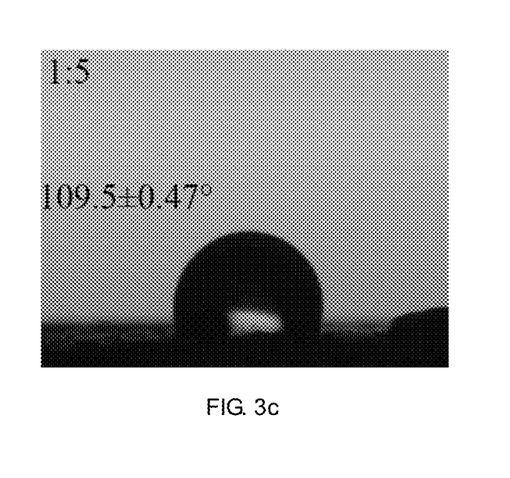

FIG. 3a-FIG. 3c are diagrams of contact angle sizes of composite nanoparticles in different ratios in the above embodiment respectively. From FIG. 3a to FIG. 3c, it can be seen that the ratio of oxidized dextrin-curcumin complex to chitosan hydrochloride is 5:1, and the contact angle of the composite nanoparticles is close to be neutral, indicating that the composite nanoparticles can be used as a good particle emulsifier.

Figure 4A:
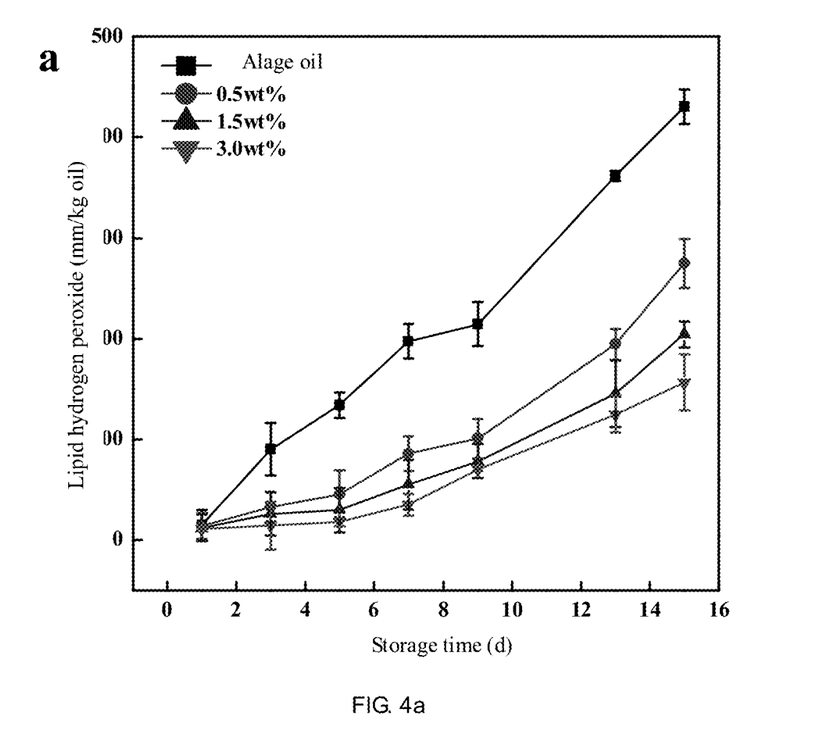
FIGS. 4a-4b are diagrams showing lipid oxidation results of $W_1/O/W_2$ double emulsion according to a typical embodiment of the present application.
Figure 4B:
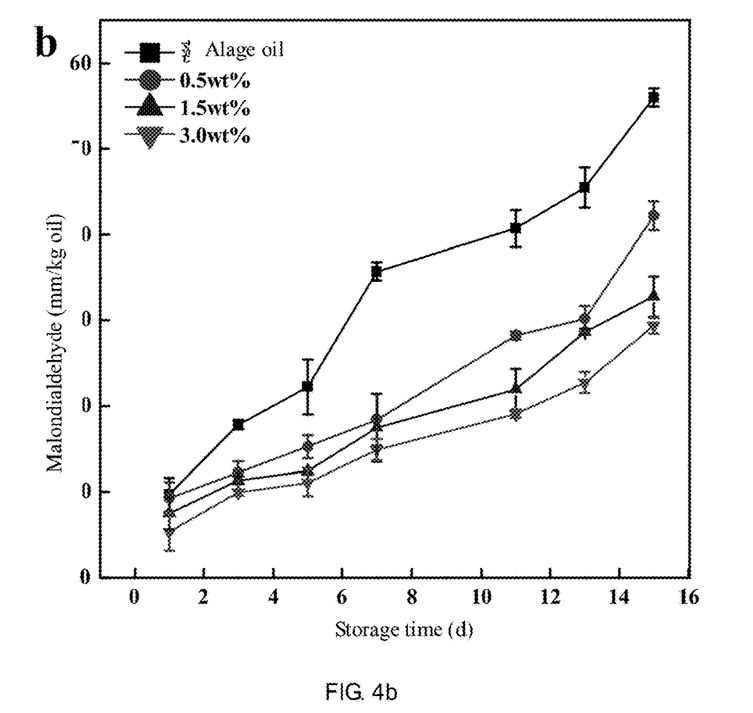

FIGS. 4a and 4b are lipid oxidation results of double emulsions in the above embodiments. It can be seen from FIGS. 4a and 4b that the lipid oxidation rate of the composite nanoparticles stabilized double emulsion is lower than that of bulk oil, indicating that the composite nanoparticles stabilized double emulsion has good antioxidant property.

Figure 5:
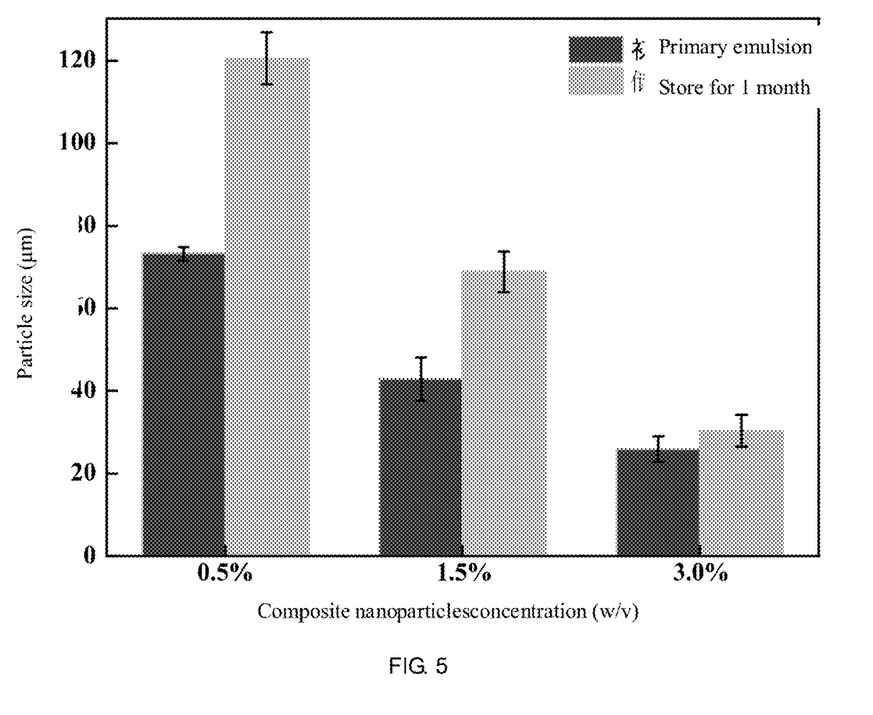
FIG. 5 is a diagram showing a storage stability result of $W_1/O/W_2$ double emulsion according to a typical embodiment of the present application.

FIG. 5 is a storage stability result of double emulsion in the above embodiments. It can be seen from FIG. 5 that the double emulsion stabilized by the composite nanoparticles has good storage stability and increases the concentration of the composite nanoparticles, and the storage stability of double emulsion is increased.

In summary, the $W_1/O/W_2$ double-emulsion gel obtained by the above technical solution of the present application has good oxidation resistance and long-term storage stability (180 days), and has wide applications in the fields of nutrition protection, drug delivery, cosmetic preparation and the like.

All aspects, embodiments, features and examples of the present application shall be deemed to be illustrative in all aspects and are not intended to limit the present application. The scope of the present application is only defined by claims. Without departing from the spirit and scope of the present application, those skilled in the art will understand other embodiments, modifications and uses.

The use of headings and sections in the present application does not mean to limit the present application; each section may be applied to any aspect, embodiment or feature of the present application.

In the whole application, where the composition is described as having, comprising or including a specific component or the process is described as having, comprising or including a specific process step, it is expected that the composition taught in the present application also substantially consists of or consists of the described components, and the process taught in the present application also substantially consists of or consists of the described process steps.

It should be understood that the order of steps or the order in which specific actions are performed is not very important, as long as the instruction of the present application remains operable. In addition, two or more steps or actions can be performed at the same time.

In addition, the inventor of the present application performs experiments with reference to the above embodiments 1-3 and by using other raw materials, process operations and process conditions described in this specification, and relatively ideal results are obtained.

Although the present application has been described with reference to illustrative embodiments, it will be understood by those skilled in the art that various other changes, omissions and/or additions may be made without departing from the spirit and scope of the present application and that the elements of the embodiments may be replaced by substantial equivalents. In addition, many modifications may be made without departing from the scope of the present application so that specific circumstances or materials are adapted to the teaching of the present application. Therefore, it is not intended to limit the present application to the specific embodiments disclosed for the implementation of the present application, but to allow the present application to include all embodiments belonging to the scope of the appended claims. In addition, unless specifically stated, any use of terms first, second and the like does not indicate any order or importance, but the terms first, second and the like are used to distinguish one element from another element.

What is claimed is:

1. A preparation method of dual-function starch-based composite nanoparticles, comprising:
   hydrolyzing starch to form starch hydrolyzate, thereby obtaining linear dextrin;
   grading the linear dextrin by using an alcohol-alcohol gradient precipitation method to obtain linear dextrin having homogeneous molecular weight distribution;
   oxidizing the linear dextrin by adopting a TEMPO/NaClO/NaBr oxidation system to obtain oxidized dextrin;
   performing complex reaction on a first mixed system containing oxidized dextrin and curcumin to form an oxidized dextrin-curcumin complex; and
   forming an oxidized dextrin-curcumin/chitosan hydrochloride composite nanoparticles from the oxidized dextrin-curcumin complex and chitosan hydrochloride through electrostatic complexing action, so as to obtain the dual-function starch-based composite nanoparticles, and the dual-function starch-based composite nanoparticles are preferably of a sphere shape and has a particle size of 285.3 nm~848.6 nm.

2. The preparation method according to claim 1, comprising: hydrolyzing starch by using α-amylase and pullulanase and grading via alcohol-alcohol gradient precipitation to obtain linear dextrin having homogeneous molecular weight distribution; preferably, the preparation method specifically comprising: heating and gelatinizing corn starch, firstly adding α-amylase in an acetate solution environment, hydrolyzing for 1~2 h at 50~60° C., then heating to 100~110° C. to carry out enzyme deactivation for 10~20 min, then cooling to 50~60° C., adding pullulanase to carry out de-branching treatment for 3~4 h, finally, carrying out enzyme deactivation on the obtained starch hydrolyzate, and then carrying out centrifugation, rotary evaporation and vacuum freeze drying to obtain linear dextrin, wherein preferably, the corn starch particularly comprises any one of high straight-chain corn starch, common corn starch and waxy corn starch or a combination of more than two thereof; particularly preferably, the addition amount of α-amylase in each gram of the corn starch is 2 U~6 U of enzyme unit, and the addition amount of pullulanase is 20 U~50 U of enzyme unit; particularly preferably, the hydrolysis degree of the starch hydrolyzate is 18.2~25.3%;

preferably, the preparation method comprising: slowly adding ethanol into linear dextrin dispersion liquid under the condition of continuous stirring so that the final concentration of ethanol is 10%~60%, and then storing for 24~28 h at 4~6° C., and centrifuging to obtain linear dextrin having homogeneous molecular weight distribution, wherein preferably, the polymerization degree of the linear dextrin is 20~68; preferably, the molecular weight of the linear dextrin is 3.35~10.9 KDa.

3. The preparation method according to claim 1, specifically comprising:
   providing a mixed solution containing TEMPO, NaBr and water;
   mixing the mixed solution with the linear dextrin, adjusting the pH value of the second mixed system to 10~10.75, then adding NaClO and keeping the pH value of the second mixed system unchanged, wherein the obtained oxidized dextrin is precipitated when the oxidization degree of the linear dextrin is 30~90%;
   preferably, the molar ratio of the glucose unit to TEMPO in the linear dextrin is 1:(0.01~0.02);
   preferably, the molar ratio of the glucose unit to NaBr in the linear dextrin is 1:(0.1~0.3);
   preferably, the oxidization position of the oxidized dextrin is the C6 site of hydroxyl of dextrin; preferably, the mass ratio of the linear dextrin to NaClO is (25~70):100; preferably, the oxidization degree of the oxidized dextrin is 30%~90%.

4. The preparation method according to claim 1, specifically comprising:
providing ethanol solution containing curcumin;
providing water dispersion liquid containing the oxidized dextrin, heating for 30~45 min at 90~100° C., and then cooling to 65~80° C.;
uniformly mixing the ethanol solution containing curcumin with the water dispersion liquid containing the oxidized dextrin to form the first mixed system, carrying out complex reaction for 2~4 h at 65~80° C., and then posttreating to obtain an oxidized dextrin-curcumin complex;
preferably, the concentration of curcumin in the ethanol solution containing curcumin is 4~6 mg/mL;
preferably, the concentration of the oxidized dextrin in the water dispersion liquid containing the oxidized dextrin is 8~12 mg/mL;
preferably the load capacity of curcumin in the oxidized dextrin-curcumin complex is 12 μg/mg~35 μg/mg, and the complexing rate is 8%~25%.

5. The preparation method according to claim 1, specifically comprising: uniformly mixing the oxidized dextrin-curcumin complex with chitosan hydrochloride for 30~45 min in a mass ratio of (1:5)~(5:1) in a reaction system of 20~25° C. and pH of 4~4.5, and forming an oxidized dextrin-curcumin/chitosan hydrochloride composite nanoparticles through electrostatic complexing action.

6. A preparation method of a double-emulsion gel, comprising:
preparing a dual-function starch-based composite nanoparticles by using the method according to claim 1;
uniformly mixing chloride, gelatin or ethanol or glucose with water to form a first aqueous phase solution, and uniformly mixing the first aqueous phase solution with an oil phase component to form primary emulsion;
uniformly mixing a second aqueous phase solution containing the dual-function starch-based composite nanoparticles with the primary emulsion by using high pressure homogenization and microfluidization technologies to obtain double emulsion containing gel polysaccharide; and
carrying out water bath treatment on the double emulsion containing the gel polysaccharide, adding $Ca^{2+}$, and cooling to obtain double-emulsion gel.

7. The preparation method according to claim 6, comprising: shearing the mixed solution of the primary emulsion and the second aqueous phase solution by using the high pressure homogenization technology to form crude double emulsion, then further homogenizing the crude double emulsion for 3~5 times under 103.4~121 MPa by using the high-pressure microfluidization technology to obtain the double emulsion, wherein preferably, the volume ratio of the primary emulsion to the second aqueous phase solution is (1:9)~(5:5); preferably, the concentration of the dual-function starch-based composite nanoparticles in the second aqueous phase solution is 0.5~3 wt %; preferably, gel polysaccharide in the double emulsion containing gel polysaccharide is any one of gellan gum, konjac glucomannan, sodium alginate and pectin or a combination of more than two thereof; particularly preferably, the concentration of the gel polysaccharide in the double emulsion containing the gel polysaccharide is 2~8 wt %;
and/or, the chloride comprises any one of sodium chloride, potassium chloride and magnesium chloride or a combination of more than two thereof;
and/or, the volume ratio of the oil phase component to the first aqueous phase solution is (2:8)~(5:5);
and/or, the preparation method comprises: dissolving polyglycerol *Ricinus communis* alcohol ester or soybean lecithin into an oil phase solvent and heating and stirring at 55~60° C. for 10-20 min to prepare the oil phase component wherein preferably, the oil phase solvent comprises algae oil; preferably, the quality volume ratio of the polyglycerol *Ricinus communis* alcohol ester or soybean lecithin to the oil phase solvent is (3~6):100.

8. The double-emulsion gel prepared by using the method according to claim 6, wherein preferably, the size of the droplet in the double-emulsion gel is 25.96~73.33 μm; preferably, the double-emulsion gel has viscoelasticity, self-supporting characteristics and a dense three-dimensional network structure.

* * * * *